(12) United States Patent
Kim et al.

(10) Patent No.: US 8,860,560 B2
(45) Date of Patent: Oct. 14, 2014

(54) MEDICATION HISTORY MANAGEMENT SYSTEM AND METHOD

(75) Inventors: Dae Hee Kim, Daejeon (KR); Jae Hun Choi, Daejeon (KR); Myung Eun Lim, Daejeon (KR); Soo Jun Park, Seoul (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 433 days.

(21) Appl. No.: 13/281,345

(22) Filed: Oct. 25, 2011

(65) Prior Publication Data

US 2012/0126958 A1 May 24, 2012

(30) Foreign Application Priority Data

Nov. 22, 2010 (KR) .......................... 10-2010-0116297

(51) Int. Cl.
*G08B 1/00* (2006.01)
*G06F 19/00* (2011.01)
*A61J 7/04* (2006.01)
*G07F 17/00* (2006.01)
*A61J 7/00* (2006.01)

(52) U.S. Cl.
CPC .............. *A61J 7/0481* (2013.01); *A61J 7/0084* (2013.01); *G06F 19/3462* (2013.01); *A61J 2007/0463* (2013.01); *G07F 17/0092* (2013.01)
USPC ....................... 340/309.7; 340/539.12; 368/10

(58) Field of Classification Search
USPC ............... 340/539.12, 539.29, 286.07, 309.7, 340/309.16; 128/903, 904, 205.23; 307/116; 706/10; 700/236; 221/2, 4, 7; 206/534; 705/3; 702/177; 368/10
See application file for complete search history.

(56) References Cited

U.S. PATENT DOCUMENTS

| 6,421,650 | B1 * | 7/2002 | Goetz et al. ........................ 705/3 |
| 7,978,564 | B2 * | 7/2011 | De La Huerga ................ 368/10 |
| 2007/0088664 | A1 * | 4/2007 | Nakano et al. ................... 706/10 |
| 2012/0038226 | A1 * | 2/2012 | Tran et al. ...................... 307/116 |

FOREIGN PATENT DOCUMENTS

KR       1020060077539 A       7/2006

OTHER PUBLICATIONS

Tamara L. Hayes et al., "An Electronic Pillbox for Continuous Monitoring of Medication Adherence", Proceedings of the 27th Annual International Conference of the IEEE Engineering in Medicine and Biology Society, Aug. 30-Sep. 3, 2006, New York, NY.

* cited by examiner

*Primary Examiner* — Brent Swarthout (57) ABSTRACT

The present invention discloses a medication history management system and method. The medication management system includes: a mobile terminal; a medicine storage apparatus which is operably connected to the mobile terminal and stores medicines; and a medication management server which is connected to the mobile terminal via a network, provides a medicine loading request message for requesting a user to load a medicine in the medicine storage apparatus to the user through the mobile terminal when the user who must take the medicine will go out, and provides a medication request message for requesting the user to take the medicine stored in the medicine storage apparatus to the user through the mobile terminal when it is time to take the medicine.

17 Claims, 5 Drawing Sheets

PRESCRIPTION NO : 1234567

| TIME | 2010.08.01 MORNING | 2010.08.01 AFTERNOON | 2010.08.01 EVENING | 2010.08.02 MORNING | 2010.08.02 AFTERNOON |
|---|---|---|---|---|---|
| MEDICATION INFORMATION | NOT-TAKEN | TAKEN | OUTING | OUTING | OUTING |
| STORAGE BOX NO. | | | 1 | 2 | 3 |
| PROCESS RESULT | 1 | 1 | 0 | 0 | 0 |

FIG. 6B

PRESCRIPTION NO : 1234567

| TIME | 2010.08.01 MORNING | 2010.08.01 AFTERNOON | 2010.08.01 EVENING | 2010.08.02 MORNING | 2010.08.02 AFTERNOON |
|---|---|---|---|---|---|
| MEDICATION INFORMATION | NOT-TAKEN | TAKEN | TAKEN | OUTING | OUTING |
| STORAGE BOX NO. | | | | 2 | 3 |
| PROCESS RESULT | 1 | 1 | 1 | 0 | 0 |

MEDICATION HISTORY MANAGEMENT SYSTEM AND METHOD

CROSS-REFERENCE TO RELATED PATENT APPLICATION

This application claims the benefit of Korean Patent Application No. 10-2010-0116297, filed on Nov. 22, 2010, in the Korean Intellectual Property Office, the disclosure of which is incorporated herein in its entirety by reference.

BACKGROUND OF THE INVENTION

1. Field of the Invention

The present invention relates to a medication history management system and method.

2. Description of the Related Art

In general, there are very few people who do not take a medicine at least once in their lifetime, except for some particularly healthy people, and in the case of certain diseases, patients may be required to be on medication for their entire life.

The intended effects of medication can only be seen when the medication is taken at regular intervals based on its composition and effective duration. As this can be quite troublesome, the intervals are adjusted to match ordinary people's life rhythms as such as possible. Thus, the medicine is usually taken at times such as after waking up, before meals, after meals, before going to bed, etc.

However, in today's fast-paced modern society, it is not so easy for people to remember their medicine when they go out, and to take it at the recommended times without sometimes forgetting.

Moreover, if people forget to bring their medicine when they go out or, for whatever reason, fail to take it at the recommended time, the effects are reduced and, in some cases, it also leads to misuse of medicine by continuing to take it beyond the intended period of medication.

In other words, in the case of people on long-term medication, when a paper bag is used and no instructions for taking the medication are recorded on the bag, it is easy to miss a dose. Also, when travelers or other active people carry their medication in their pockets, the bag may get damaged and the medicine may fall out and get mixed up, or the medicine may come in contact with other substances inside the pocket, rendering it unsanitary. Thus, there are many cases where patients on long-term medication cannot take their medication at the proper times and omit or skip a dose, thereby causing their condition to deteriorate.

Nowadays, there are inventions such as clocks with alarms that let people know when it is time to take their medication, pill cases that can keep track of doses, etc., but there is nothing convenient and economical enough to carry around outside.

SUMMARY OF THE INVENTION

The present invention has been made in an effort to solve the above-described problems associated with prior art, and an object of the present invention is to provide a medication history management system and method, which can provide a medication request message to a user in a simple manner even when a chronic patient on long-term medication goes out or travels.

According to an aspect of the present invention to achieve the above object of the present invention, there is provided a medication history management system comprising: a mobile terminal; a medicine storage apparatus which is operably connected to the mobile terminal and stores medicines; and a medication management server which is connected to the mobile terminal via a network, provides a medicine loading request message for requesting a user to load a medicine in the medicine storage apparatus to the user through the mobile terminal when the user who must take the medicine will go out, and provides a medication request message for requesting the user to take the medicine stored in the medicine storage apparatus to the user through the mobile terminal when it is time to take the medicine.

According to another aspect of the present invention to achieve the above object of the present invention, there is provided a medication history management method implemented in a medication history management system which comprises a mobile terminal, a medicine storage apparatus operably connected to the mobile terminal and including a plurality of storage boxes, each storing the medicine, and a medication management server for managing a medication history, the method comprising: providing a medicine loading request message for requesting a user to load a medicine in the medicine storage apparatus to the user through the mobile terminal when the user who must take the medicines will go out; and providing a medication request message for requesting the user to take the medicine stored in the medicine storage apparatus to the user through the mobile terminal when it is time to take the medicine.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention. Like numbers refer to like elements throughout the description of the figures.

It will be understood that, although the terms first, second, A, B etc. may be used herein to describe various elements, these elements should not be limited by these terms. These terms are only used to distinguish one element from another. For example, a first element could be termed a second element, and similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

Unless otherwise defined, all terms, including technical and scientific terms, used herein have the same meaning as commonly understood by one of ordinary skill in the art to which this invention pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

Figure 1:
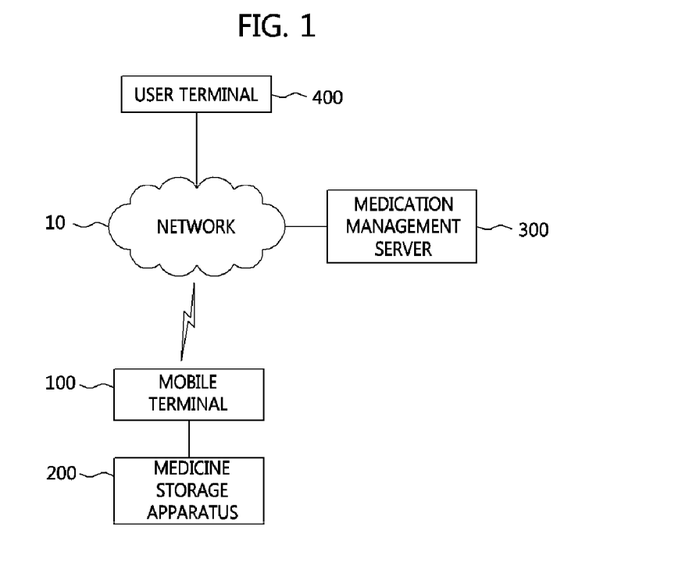
FIG. 1 is a diagram showing the configuration of a medication history management system using a mobile terminal in accordance with an exemplary embodiment of the present invention.

FIG. 1 is a diagram showing the configuration of a medication history management system using a mobile terminal in accordance with an exemplary embodiment of the present invention.

The medication history management system according to the present invention is to assist a user to take a medicine when the user goes out or travels.

Referring to FIG. 1, the medication history management system comprises a mobile terminal 100, a medicine storage apparatus 200, a medication management server 300, and a user terminal 400.

The mobile terminal 100 comprises a smart phone, a portable mobile phone, etc. The medicine storage apparatus 200 comprises a plurality of storage boxes, each storing a medicine, detects whether the medicine stored in each of the storage boxes exists therein, and outputs the result. Moreover, the medicine storage apparatus 200 is connected to the mobile terminal 100 to communicate with the mobile terminal 100. In this case, the medicine storage apparatus 200 is connected to the mobile terminal 100 by wire.

The user terminal 400 means a personal computer (PC) connectable to the Internet. The user terminal 400 is not an essential component of the present invention, and the mobile terminal 100 may perform the role of the user terminal 400.

The medication management server 300 may be a web server, for example. The medication management server 300 is connected to the mobile terminal 100 via a network 10 to notify a user through the mobile terminal 100 to load a medicine in the medicine storage apparatus 200 when the user who must take the medicine will go out.

In detail, the medication management server 300 determines whether outing information of the user is input. The outing information of the user may be input to the medication management server 300 through the mobile terminal 100 or the user terminal 400 by the user.

Otherwise, another medicine storage apparatus (not shown) connected to the medication management server 300 may be included in the medication history management system. In this case, when the user takes out the medicine stored in another medicine storage apparatus for an outing, another medicine storage apparatus notifies the medication management server 300 about the medicine taken out by the user. Accordingly, the medication management server 300 may designate the medicines taken out by the user for the outing as medicines to be taken during the outing. That is, the medication management server 300 may input the outing information of the user based on the medicines taken out by the user for the outing.

The medication management server 300 may transmit a medicine loading request message to the mobile terminal 100 when the outing information of the user is input. Moreover, the medication management server 300 may transmit a medication request message to the mobile terminal 100 when it is time for the user to take the medicine.

When the medicine loading request message or the medication request message is received, the mobile terminal 100 checks whether it is connected to the medicine storage apparatus 200. If the mobile terminal 100 is not connected to the medicine storage apparatus 200, the mobile terminal 100 displays a connection request message for requesting the user to connect the mobile terminal 100 to the medicine storage apparatus 200 through a display device thereof. Otherwise, the mobile terminal 100 may output the connection request message by voice through a speaker thereof.

When the mobile terminal 100 is connected to the medicine storage apparatus 200, the mobile terminal 100 transmits the medicine loading request message or the medication request message to the medicine storage apparatus 200. When the medicine loading request message or the medication request message is received, the medicine storage apparatus 200 determines whether the medicine is stored in the plurality of storage boxes.

Upon reception of the medicine loading message, if the medicine is stored in the plurality of storage boxes, the medicine storage apparatus 200 transmits medicine loading information to the medication management server 300 through the mobile terminal 100.

Upon reception of the medication request message, if the medicine does not exist in one of the plurality of storage boxes, the medicine storage apparatus 200 transmits medication information to the medication management server 300 through the mobile terminal 100.

When the medicine loading information or the medication information is received through the mobile terminal 100, the medication management server 300 updates a medication schedule of the user. For example, when the medicine loading information is received, the medication management server 300 generates schedules corresponding to the outing of the user, thereby updating the medication schedule. When the medication information is received, the medication management server 300 changes the medication information from "not-taken" to "taken" in the corresponding schedule, thereby updating the medication schedule.

The above-described medicine storage apparatus 200 will be described in more detail below.

Figure 2:
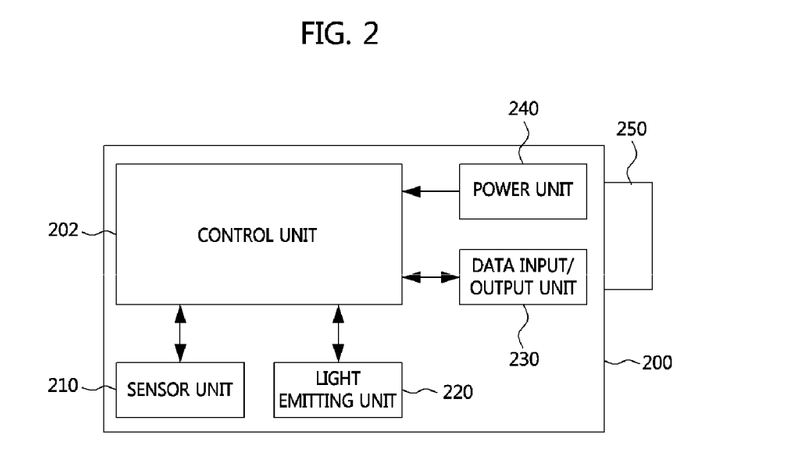
FIG. 2 is a functional block diagram of a medicine storage apparatus 200 in accordance with an exemplary embodiment of the present invention.

FIG. 2 is a functional block diagram of the medicine storage apparatus 200 in accordance with an exemplary embodiment of the present invention.

Referring to FIG. 2, the medicine storage apparatus 200 comprises a control unit 202, a sensor unit 210, a light emitting unit 220, a data input/output unit 230, a power unit 240, and a connection unit 250.

The control unit 202 transmits and receives data to and from the mobile terminal 100 through the data input/output unit 230. Moreover, the control unit 202 may enable the sensor unit 210 and the light emitting unit 220. The sensor unit 210 comprises a plurality of sensors, each disposed in each of the plurality of storage boxes provided in the medicine storage apparatus 200. Each of the plurality of sensors detects whether the medicine is stored in each of the plurality of storage boxes and provides the detection result to the control unit 202. Each sensor may be a photo interrupter, i.e., an infrared sensor.

The light emitting unit 220 comprises a plurality of light emitting devices, each disposed in each of the plurality of storage boxes. The light emitting devices may emit light or may be turned on individually under the control of the control unit 202. The control unit 202 may selectively make the light emitting devices, each disposed in each of the storage boxes storing the medicines to be taken by the user, emit light. Moreover, the control unit 202 may selectively make the light emitting devices, each disposed in an empty storage box in which the medicine is to be stored, emit light. The power unit 240 supplies power to the respective components of the medicine storage apparatus 200.

The connection unit 250 connects the medicine storage apparatus 200 to the mobile terminal 100. The power unit 240 is connected to the mobile terminal 100 through the connection unit 250 to receive power from the mobile terminal 100. Moreover, the data input/output unit 230 transmits and receives data to and from the mobile terminal 100 through the connection unit 250. Accordingly, when the medicine storage apparatus 200 is connected to the mobile terminal 100, the medicine storage apparatus 200 does not require a separate battery. As a result, the volume of the medicine storage apparatus 200 may be reduced, which makes it easy and convenient for the user to carry the medicine storage apparatus 200.

Figure 3:
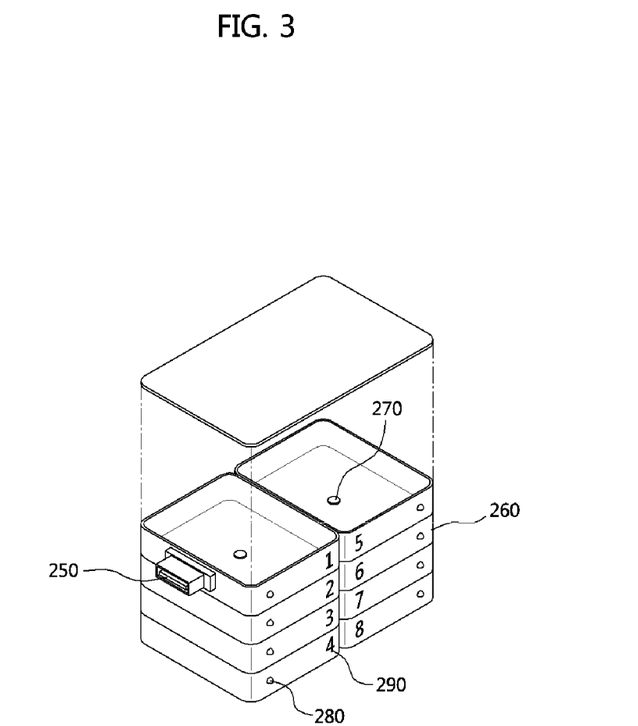
FIG. 3 is a diagram showing an exterior of a medicine storage apparatus 200 in accordance with an exemplary embodiment of the present invention.

The exterior of the medicine storage apparatus 200 having the above-described configuration is shown in FIG. 3.

FIG. 3 is a diagram showing an exterior of the medicine storage apparatus 200 in accordance with an exemplary embodiment of the present invention.

As shown in FIG. 3, the medicine storage apparatus 200 comprises a plurality of storage boxes and, in this embodiment, a total of eight storage boxes capable of storing a total of eight medicines are provided. Each storage box 260 is configured to be opened and closed like a drawer. As mentioned above, the medicine storage apparatus 200 comprises the connection unit 250 which can be docked with the mobile terminal 100 to transmit and receive data to and from the mobile terminal 100 and receive power from the mobile terminal 100. A sensor 270 for determining whether there is a medicine bag is provided in the center of each storage box 260 in the form of a drawer. When viewed from the front, a light emitting device 280 is provided on one side and a number 290 from 1 to 8 is written on the other side.

Figure 4:
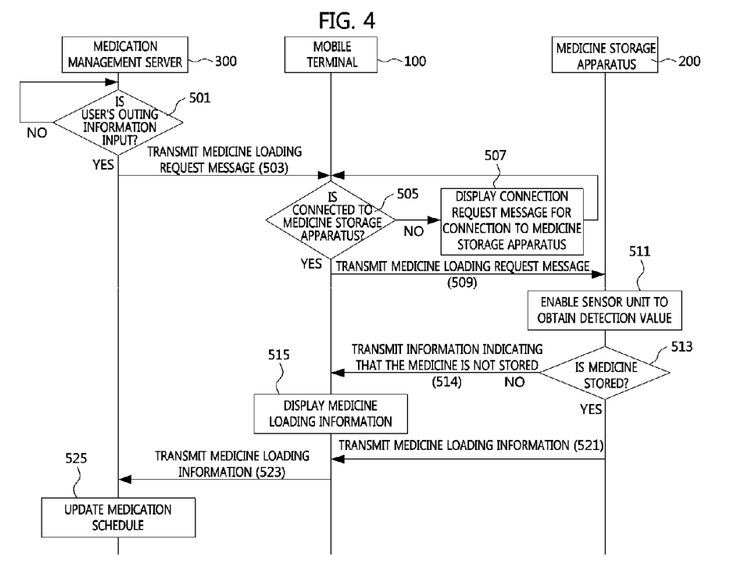
FIG. 4 shows a control flow for loading a medicine in accordance with an exemplary embodiment of the present invention.
Figure 5:
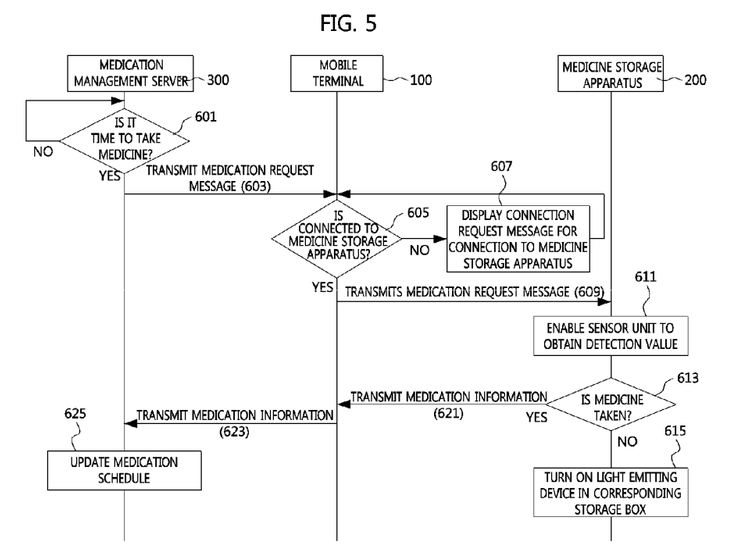
FIG. 5 shows a control flow for taking a medicine in accordance with an exemplary embodiment of the present invention.

FIG. 4 shows a control flow for loading a medicine in accordance with an exemplary embodiment of the present invention, and FIG. 5 shows a control flow for taking a medicine in accordance with an exemplary embodiment of the present invention.

Referring to FIG. 4, the medication management server 300 determines whether a user's outing information is input in step 501.

As mentioned above, according to an exemplary embodiment, the outing information of the user may be input to the medication management server 300 through the mobile terminal 100 or the user terminal 400 by the user.

According to another exemplary embodiment, another medicine storage apparatus (not shown) connected to the medication management server 300 may be included in the medication history management system. In this case, when the user takes out the medicine stored in another medicine storage apparatus for an outing, another medicine storage apparatus notifies the medication management server 300 about the medicine taken out by the user. Accordingly, the medication management server 300 may designate the medicines taken out by the user for the outing as medicines to be taken during the outing. That is, the medication management server 300 may input the outing information of the user based on the medicines taken out by the user for the outing.

When the outing information of the user is input, the medication management server 300 may transmit a medicine load request message to the mobile terminal 100. For example, the medication management server 300 may transmit a message to the effect that "Hong Gil-dong, there are four outing-medicines, please load the medicine into storage boxes No. 1 to 4". Selectively, the medication management server 300 may transmit a connection request message for requesting connection to the mobile terminal 100. As the connection request message, a message to the effect that "Please connect the mobile device to the medicine storage apparatus" may be transmitted.

When the medicine loading request message is received in step 503, the mobile terminal 100 determines whether it is connected to the medicine storage apparatus 200 in step 505. If the mobile terminal 100 is not connected to the medicine storage apparatus 200, the mobile terminal 100 may display the connection request message for requesting connection to the mobile terminal 100 through a display device thereof or output the connection request message by voice through a speaker thereof in step 507.

If the mobile terminal 100 is connected to the medicine storage apparatus 200, the mobile terminal 100 transmits the medicine loading request message to the medicine storage apparatus 200 in step 509. If the medicine loading request message is received, the medicine storage apparatus 200 enables the sensor unit 210 to obtain a detection value in step 511. As mentioned above, the medicine storage apparatus 200 comprises the plurality of storage boxes, and the sensor for detecting whether the medicine is stored is provided in each storage box. If the medicine loading request message is received, the medicine storage apparatus 200 enables the sensor unit 210 to detect whether the medicine is stored in each storage box. Then, the sensor unit 210 detects whether the medicine is stored in each storage box and outputs the result in step 513. If the medicine is not stored in the corresponding storage box, the medicine storage apparatus 200 transmits information indicating that the medicine is not stored to the mobile terminal 100 in step 514. When the information indicating that the medicine is not stored is received, the mobile terminal 100 may display the medicine loading request message to the user or output the medicine loading request message by voice in step 515.

If the medicine is stored in the corresponding storage box, the medicine storage apparatus 200 transmits medicine loading information to the mobile terminal 100 in step 521. Accordingly, the mobile terminal 100 transmits the medicine loading information to the medication management server 300 in step 523. If the medicine loading information is received, the medication management server 300 may generate schedules corresponding to the outing of the user, thereby updating a medication schedule in step 525.

Next, the control flow for taking a medicine will be described with reference to FIG. 5.

Referring to FIG. 5, the medication management server 300 determines whether it is time for the user to take the medicine in step 601. If it is time to take the medicine, the medication management server 300 transmits a medication request message to the mobile terminal 100 in step 603. For example, the medication management server 300 may transmit a message to the effect that "Hong Gil-dong, it is time to take the outing-medicine". Selectively, the medication management server 300 may transmit a connection request message for requesting connection to the mobile terminal 100. As the connection request message, a message to the effect that "Please connect the mobile device to the medicine storage apparatus" may be transmitted.

If the medication request message is received in step 603, the mobile terminal 100 determines whether it is connected to the medicine storage apparatus 200 in step 605. If the mobile terminal is not connected to the medicine storage apparatus 200, the mobile terminal 100 may display the connection request message for requesting connection to the mobile terminal 100 through a display device thereof or output the connection request message by voice through a speaker thereof in step 607.

If the mobile terminal is connected to the medicine storage apparatus 200, the mobile terminal 100 transmits the medication request message to the medicine storage apparatus 200 in step 609.

If the medication request message is received, the medicine storage apparatus 200 enables the sensor unit 210 to obtain a detection value in step 611. As mentioned above, if the medication request message is received, the medicine storage apparatus 200 enables the sensor unit 210 to detect whether the medicine is stored in the corresponding storage box, thereby obtaining the detection value.

If it is determined that the medicine is stored in the corresponding storage box in step 613, that is, if it is determined that the medicine is not taken by the user, the medicine storage apparatus 200 makes the light emitting device, which is provided in the corresponding storage box, emit light or turns on the light emitting device in step 615. In other words, the medicine storage apparatus 200 receives the medication request message from the medication management server 300 and turns on the light emitting device of the storage box storing the medicine to be taken by the user. Then, the user sees the light emitting device turned on and takes the medicine stored in the storage box. As mentioned above, whether the medicine is taken may be determined based on the value of the sensor, i.e., the photo interrupter, attached to the storage box. If the medicine is not taken by the user, the light emitting device is continuously turned on.

If it is determined that the medicine is taken by the user, that is, if it is determined that the medicine does not exist in the corresponding storage box, the medicine storage apparatus 200 disables the corresponding light emitting device (not shown).

If the medicine is not stored in the corresponding storage box, the medicine storage apparatus 200 transmits medication information to the mobile terminal 100 in step 621. The reason for this is that, if the storage box storing the medicine to be taken by the user is empty, it may be determined that the user has taken the medicine. The mobile terminal 100 transmits the mediation information to the medication management server 300 in step 623.

If the mediation information is received, the medication management server 300 changes the medication information from "not-taken" to "taken", for example, in the corresponding schedule, thereby updating the medication schedule in step 625.

Figure 6A:
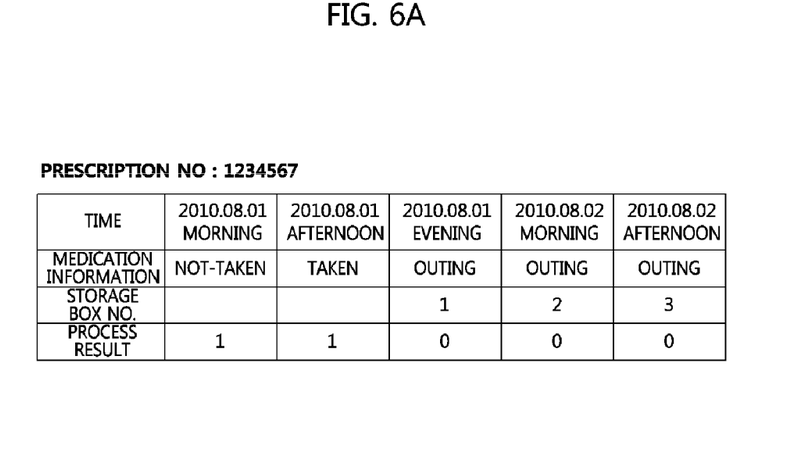
FIGS. 6A and 6B are diagrams showing examples of tables of an outing-related database of a medicine management server in accordance with exemplary embodiments of the present invention.
Figure 6B:
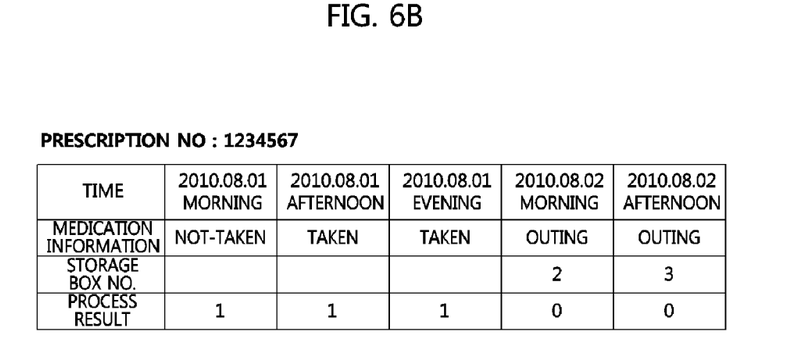

FIGS. 6A and 6B are diagrams showing examples of tables of an outing-related database of a medicine management server in accordance with exemplary embodiments of the present invention.

FIG. 6A shows the contents of the database after the medicines are stored in the storage boxes and FIG. 6B shows the contents of the database after the medicines are taken.

As shown in FIGS. 6A and 6B, the table related to the medication schedule may be provided for each prescription number. The table related to the medication schedule may include the medication time, the medication information, the number of storage box, and the process result.

The number of the storage box represents one of the numbers from 1 to 8 written on each of the storage boxes. The process result has a value of 1, and the number is changed to 0 when the medication information corresponds to the outing.

The table shown in FIG. 6A shows the contents stored in the medication management server 300 after the medicines are stored in the storage boxes, in which three medicines are taken out for the outing. The medicines are stored in storage boxes No. 1, 2 and 3. Then, the contents stored in the medication management server 300 after the user who receives an alarm in the evening of Aug. 1, 2010 takes the medicine stored in storage box No. 1 are shown in the table of FIG. 6B, in which the outing of the medication information is changed from "outing" to "taken", the number of the corresponding storage number is changed from 1 to blank, and the process result is changed 0 to 1.

As described above, according to the present invention, the user can receive the medication request message from the medication management server through the mobile terminal during an outing. Moreover, according to the present invention, the mobile terminal is connected to the medicine storage apparatus, and thus the information on the medicine to be taken by the user can be displayed on the mobile terminal. Furthermore, the medicine storage apparatus according to the present invention does not require power, and thus its volume can be reduced, which makes it easy and convenient for the user to carry the medicine storage apparatus.

While the invention has been particularly shown and described with reference to exemplary embodiments thereof, it will be understood by those of ordinary skill in the art that various changes in form and details may be made therein without departing from the spirit and scope of the invention as defined by the following claims.

What is claimed is:

1. A medication history management system comprising:
a mobile terminal;
a medicine storage apparatus, which is operably connected to the mobile terminal and stores medicines; and
a medication management server, which is connected to the mobile terminal via a network, that provides a medicine loading request message for requesting a user to load a medicine in the medicine storage apparatus to the user through the mobile terminal when the user goes out, and provides a medication request message for requesting the user to take the medicine stored in the medicine storage apparatus to the user through the mobile terminal at a time when the user is scheduled to take the medicine;

wherein the mobile terminal checks whether the mobile terminal is connected to the medicine storage apparatus if the medicine loading request message or the medication request message is received from the medication management server, and outputs a connection request message for requesting the user to connect the mobile terminal to the medicine storage apparatus when the mobile terminal is not connected to the medicine storage apparatus.

2. The system of claim 1, wherein the mobile terminal outputs the medicine loading request message or the medication request message to the medicine storage apparatus if the mobile terminal is connected to the medicine storage apparatus.

3. The system of claim 2, wherein the medicine storage apparatus comprises:

a plurality of storage boxes, each storing the medicine;

a plurality of sensors, each disposed in each of the storage boxes and detecting whether the medicine is stored in the corresponding storage box; and a plurality of light emitting devices, each disposed in each of the storage boxes.

4. The system of claim 3, wherein the medicine storage apparatus enables the plurality of sensors to detect whether the medicine is stored in the storage boxes if the medicine loading request message is received from the mobile terminal and, if there is a storage box in which the medicine is not stored, turns on the light emitting device provided in the corresponding storage box.

5. The system of claim 3, wherein the medicine storage apparatus enables the plurality of sensors to detect whether the medicine is stored in the storage boxes if the medicine loading request message is received from the mobile terminal and, if the medicine is stored in the corresponding storage box, transmits medicine loading information to the mobile terminal, and wherein the mobile terminal transmits the medicine loading information to the medication management server.

6. The system of claim 5, wherein the medication management server updates a medication schedule associated with the user if the medicine loading information is received from the mobile terminal.

7. The system of claim 3, wherein the medicine storage apparatus enables the plurality of sensors to detect whether the medicines stored in the storage boxes exist if the medication request message is received from the mobile terminal and, if the medicine to be taken by the user is stored in the corresponding storage box, turns on the light emitting device provided in the corresponding storage box.

8. The system of claim 3, wherein the medicine storage apparatus enables the plurality of sensors to detect whether the medicines stored in the storage boxes exist if the medication request message is received from the mobile terminal and, if the medicine to be taken by the user is not stored in the corresponding storage box, transmits medication information to the mobile terminal, and wherein the mobile terminal transmits the medication information to the medication management server.

9. The system of claim 8, wherein the medication management server updates a medication schedule associated with the user if the medication information is received from the mobile terminal.

10. A medication history management method implemented in a medication history management system, which comprises a mobile terminal, a medicine storage apparatus operably connected to the mobile terminal and including a plurality of storage boxes, each storing the medicine, and a medication management server for managing a medication history, the method comprising:

providing a medicine loading request message for requesting a user to load a medicine in the medicine storage apparatus to the user through the mobile terminal when the user goes out;

providing a medication request message for requesting the user to take the medicine stored in the medicine storage apparatus to the user through the mobile terminal at a time when the user is scheduled to take the medicine;

checking, at the mobile terminal, whether the mobile terminal is connected to the medicine storage apparatus if the medicine loading request message or the medication request message is received; and outputting, at the mobile terminal, a connection request message for requesting the user to connect the mobile terminal to the medicine storage apparatus when the mobile terminal is not connected to the medicine storage apparatus.

11. The method of claim 10, further comprising outputting, at the mobile terminal, the medicine loading request message or the medication request message to the medicine storage apparatus if the mobile terminal is connected to the medicine storage apparatus.

12. The method of claim 11, further comprising:

enabling, at the medicine storage apparatus, a plurality of sensors, each disposed in each of the storage boxes and detecting whether the medicine is stored in the corresponding storage box, to detect whether the medicines stored in the storage boxes exist if the medicine loading request message is received from the mobile terminal; and if there is a storage box in which the medicine is not stored, turning on, at the medicine storage apparatus, a light emitting device provided in the corresponding storage box.

13. The method of claim 11, further comprising:

enabling, at the medicine storage apparatus, a plurality of sensors, each disposed in each of the storage boxes and detecting whether the medicine is stored in the corresponding storage box, to detect whether the medicine is stored in the storage boxes if the medicine loading request message is received from the mobile terminal;

if the medicine is stored in the corresponding storage box, transmitting, at the medicine storage apparatus, medicine loading information to the mobile terminal; and transmitting, at the mobile terminal, the medicine loading information to the medication management server.

14. The method of claim 13, further comprising updating, at the medication management server, a medication schedule associated with the user if the medicine loading information is received from the mobile terminal.

15. The method of claim 11, further comprising:

enabling, at the medicine storage apparatus, a plurality of sensors, each disposed in each of the storage boxes and detecting whether the medicine is stored in the corresponding storage box, to detect whether the medicines stored in the storage boxes exist if the medication request message is received from the mobile terminal; and if the medicine to be taken by the user is stored in the corresponding storage box, turning on, at the medicine storage apparatus, a light emitting device provided in the corresponding storage box.

16. The method of claim 11, further comprising:
enabling, at the medicine storage apparatus, a plurality of sensors, each disposed in each of the storage boxes and detecting whether the medicine is stored in the corresponding storage box, to detect whether the medicines stored in the storage boxes exist if the medication request message is received from the mobile terminal;
if the medicine to be taken by the user is not stored in the corresponding storage box, transmitting, at the medicine storage apparatus, medication information to the mobile terminal, and
transmitting, at the mobile terminal, the medication information to the medication management server.

17. The method of claim 16, further comprising updating, at the medication management server, a medication schedule associated with the user if the medication information is received from the mobile terminal.

* * * * *